United States Patent [19]

Kawahara et al.

[11] 4,155,124

[45] May 22, 1979

[54] BURNT CERAMIC BONE IMPLANT

[75] Inventors: Haruyuki Kawahara, Moriguchi; Masaya Hirabayashi, Kyoto; Yoshiteru Hamano, Otsu; Yoshimasa Goto, Kyoto, all of Japan

[73] Assignee: Kyoto Ceramic Co., Ltd., Japan

[21] Appl. No.: 872,684

[22] Filed: Jan. 26, 1978

Related U.S. Application Data

[63] Continuation of Ser. No. 790,249, Apr. 25, 1977, abandoned, which is a continuation of Ser. No. 684,051, May 6, 1966, abandoned, which is a continuation of Ser. No. 546,023, Jan. 31, 1975, abandoned, which is a continuation-in-part of Ser. No. 524,557, Nov. 18, 1974, abandoned.

[51] Int. Cl.² .................... A61F 1/24; A61C 13/30
[52] U.S. Cl. .................................. 3/1.9; 128/92 B; 128/92 C; 32/10 A; 106/57; 106/73.2; 106/73.4

[58] Field of Search ............... 3/1, 1.9–1.913; 128/92 C, 92 CA, 92 R, 92 B; 32/10 A; 106/73.2, 73.33, 73.4, 57, 65

[56] References Cited

U.S. PATENT DOCUMENTS

| 3,725,094 | 4/1973 | Levy et al. | 106/73.4 X |
| 3,776,744 | 12/1973 | Clendenen | 106/73.4 |
| 3,784,388 | 1/1974 | King et al. | 106/73.4 |
| 3,837,870 | 9/1974 | Recasens et al. | 106/57 |

FOREIGN PATENT DOCUMENTS 1083769  9/1967  United Kingdom ............... 128/92 C Primary Examiner—Ronald L. Frinks
Attorney, Agent, or Firm—Spensley, Horn & Lubitz

[57] ABSTRACT

This invention is directed to a burnt ceramics composition of matter for an endosseous implant to be inserted in the bone tissue of a living body. The composition of matter consists of 95–50% of $Al_2O_3$ and 5–50% of more than one compound selected from the group consisting of $ZrO_2$, $La_2O_3$ and $Y_2O_3$.

1 Claim, No Drawings

BURNT CERAMIC BONE IMPLANT

This application is a continuation of application Ser. No. 790,249 filed Apr. 25, 1977, now abandoned, which is a continuation of application Ser. No. 684,051 filed May 6, 1966, now abandoned, which is a continuation of application Ser. No. 546,023 filed Jan. 31, 1975, now abandoned, which is a continuation-in-part of application Ser. No. 524,557 filed Nov. 18, 1974, now abandoned.

BACKGROUND OF THE INVENTION

1. Field of the Invention

This invention relates to a burnt ceramics composition of matter adapted for use as artificial bone in the fields of dentistry, oral surgery and orthopedics.

2. Description of the Prior Art

In accordance with the development of bio-engineering, implantation of artificial bio-material into the bone tissue of a living body has become popular of late. For instance, a dental implantation technique has been developed wherein in order to supplement the loss of natural teeth by artificial teeth, an implant is implanted or inserted in the endosseous or subperiosteal portion of the jaw as a substitute for a clasp abutment tooth of a cantilevered bridge or an abutment tooth of a fixed bridge. The artificial tooth or teeth thus implanted by the implantation technique is called an implant crown, an implant bridge or an implant denture.

The term "implant" as used herein has two meanings, for example, to denote the "implant (element) itself" and also to denote the act of "inserting the implant (element) into the bone tissue of the living body".

As for the material of an implant, metal is conventionally used, predominantly the molded type (ready-made type) of the blade or screw variety or a casted type adapted individually for the endosseous portion of the jaw. In the selection of the metal it is of great importance to take into consideration the so-called "compatibility" between the implant element and the surrounding tissues and especially the compatibility between the surrounding tissues and the surface of a post portion of the implanted artificial tooth. For this purpose, titanium, cobalt-chromium alloys, tantalum, nickel-chromium alloys, iron-nickel-chromium alloys and the like are used. However, these materials have a common drawback in that they can be easily ionized by saliva, secretions in the mouth, food, body fluid, blood and the like, thereby affecting surrounding bone tissues and soft tissues. For instance, in the case where a cobalt-chromium alloy or titanium is used for an implant and the cells surrounding the implant are not compatible with the alloy or metal, it is an essential defect that the surrounding tissues are not adhesive to the implant.

In consideration of this defect, there has been an attempt to use stable plastic materials or ceramic materials instead of easily ionized metals. However, the plastic materials may deteriorate by depolymerization in the living body so that they are not only useless as an implant but also there is a possibility that they may be a carcinogenic factor seriously affecting the surrounding tissues. On the other hand, ceramics are very stable chemically as well as physically and therefore it is the most suitable material to avoid the above-mentioned defect. However, in an X-ray photograph for postoperative medical treatment, the ceramic implant is transparent to the X-rays making radiographic treatment almost impossible and impairing the observation of the boundaries between the implant and the surrounding tissues. This is a great obstacle in many cases which are concerned with examining the growing conditions of the surrounding tissues with respect to the implant, and which are concerned with inspecting postoperative development such as locating that portion of the implant which is embedded in the jaw bone.

BRIEF SUMMARY OF THE INVENTION

Accordingly, the primary object of the present invention is to provide a burnt ceramics composition of matter for an implant which is physically, chemically and biologically stable, having such mechanical strength as to be sufficiently tolerant to repeated external forces, such as the biting stresses from artificial teeth which may be added to the implant after insertion thereof, and also be radiographically opaque.

Another object of the present invention is, in conjunction with the above-mentioned object, to provide a burnt ceramics composition of matter for an implant in which the radiographically opaque feature produces a clear white picture of the implant on an X-ray transparency, thereby facilitating easy determination of that portion of the inserted implant which is embedded in the jaw or other bone tissues.

Still another object of the present invention is to provide an implant having all of the above features.

Other objects and advantages of the invention will be apparent from the following description taken in connection with the accompanying embodiment.

DETAILED DESCRIPTION OF THE PREFERRED EMBODIMENTS

The final composition range after burning of the burnt ceramics composition of matter for an endosseous implant according to the present invention is composed of 95 to 50% of $Al_2O_3$ and pin, 5 to 50% of more than one compound selected from the group consisting of $ZrO_2$, $La_2O_3$ and $Y_2O_3$. $Al_2O_3$ has the greatest mechanical strength to compressive bending and tensile stresses among the ceramics and at the same time is sufficiently resistant to each of the above mentioned external forces. This strength is required of the implant, especially against biting stresses. In addition, it is chemically, physically and biologically stable. Therefore, the implant of the present invention having $Al_2O_3$ as the main content is sufficiently rigid and is mechanically, physically and chemically stable. However, since $Al_2O_3$ ceramic alone is transparent to X-rays, the radiographically opaque constituent, which consists of more than one compound selected from the group of $ZrO_2$, $La_2O_3$ and $Y_2O_3$, is indispensably included, according to the present invention, in $Al_2O_3$ ceramic. These metal oxides can be sintered together with $Al_2O_3$ ceramic to form a uniform ceramics composition of matter by means of a high temperature chemical reaction through which $Al_2O_3$ is sintered to the above ceramics. The composition range of the primary ceramic, $Al_2O_3$, and radiographically opaque ceramics, $ZrO_2$, $La_2O_3$ and $Y_2O_3$, is defined as above-mentioned for the following reason. If $Al_2O_3$ is below 50%, the mechanical strength of the composite is reduced and the ceramics becomes brittle. If the proportion of radiographically opaque ceramics is below 5%, the radiographic opacity is not sufficiently high and thereby results in an obscure radiograph. The most preferable range is 90 to 80% of $Al_2O_3$ and 10 to 20% of more than one compound selected from the group consisting of $ZrO_2$, $La_2O_3$ and $Y_2O_3$. In order to obtain the composition of matter of the present invention, $Al_2O_3$ and more than one compound selected from the group, $ZrO_2$, $La_2O_3$ and $Y_2O_3$, are mixed at the predetermined stoichiometrical ratio so that the composition range after burning may be identical to the aforementioned. The mixture is then molded into the shape of an implant, especially of the screw, blade or pin variety, and burnt at the temperature of about 1,600° C. thereby forming a composite of ceramics. A burning accelerator for $Al_2O_3$, such as BaO, CaO, MgO, may be included in the preferred ceramic composition. The content range of the accelerator, if added, is fixed at less than 10% of the final range of the burnt composition of matter. If it exceeds 10%, it may adversely affect the mechanical strength and the radiographic opacity of the ceramics. Therefore, the above described range of composition does not exclude the addition of a burning accelerator for $Al_2O_3$, such as BaO, CaO, MgO, in proportions less than 10%. However, addition of a burning accelerator for $Al_2O_3$ may be entirely optional.

The examples of the present invention are put forth below.

Composition: Nine flat rectangular (18×4×1 mm) test pieces, (A) to (I), variously having the composition defined in the present invention, the semi-invention or a contrast example are irradiated in the same manner as would be the case in a medical treatment. Test pieces (A) through (F) have a composition within the definition of the present invention; test pieces (G) and (H) have a composition close to but outside the definition of the present invention; and test piece (I) has a composition clearly and distinctly outside the present invention. The results are described below.

| TEST PIECE | SPECIES | COMPOSITION (WEIGHT%) |
|---|---|---|
| (A) | Present invention | $Al_2O_3$ 95% + $ZrO_2$ 5% |
| (B) | " | $Al_2O_3$ 90% + $ZrO_2$ 10% |
| (C) | " | $Al_2O_3$ 80% + $ZrO_2$ 20% |
| (D) | Present invention | $Al_2O_3$ 60% + $ZrO_2$ 40% |
| (E) | " | $Al_2O_3$ 80% + $Y_2O_3$ 20% |
| (F) | " | $Al_2O_3$ 80% + $Y_2O_3$ 10% + $La_2O_3$ 10% |
| (G) | Semi-invention | $Al_2O_3$ 97% + $ZrO_2$ 3% |
| (H) | " | $Al_2O_3$ 96% + $Y_2O_3$ 4% |
| (I) | Contrast example | $Al_2O_3$ 100% |

Results: Each piece listed above was subjected to the same radiation test, and a dry plate picture was obtained therefrom. The test piece (I) of alumina ceramics alone is totally transparent to X-rays. The test pieces (G) and (H) of the semi-invention, the composition range of which is outside of that of the present invention with respect to the proportion of $ZrO_2$ and $Y_2O_3$, but nearly within the invention in regard to the proportion of $Al_2O_3$, has more radiographic opacity than test piece (I) owing to the proportion of $ZrO_2$ and $Y_2O_3$. However, they are still not sufficiently radiographically opaque since they appear grey in a transparency. In contrast thereto, the preferred ceramics composition clearly exhibits radiographic opacity showing almost as a clean white in a transparency. Accordingly, the implant of the present invention enables one to clearly locate that portion of an implant embedded in the jaw bone by means of radiographic inspection.

As the invention is understood from the above description and embodiments together with the examples of various implants used in the field of dentistry and oral surgery, the present invention may be seen to have the following advantages:

(a) The implant portion can be clearly determined by X-ray inspection owing to radiographic opacity of the implant in the jaw bone.

(b) Similarly, the progressive change of the bone tissues arround the implant after the passage of time can be recorded by X-ray transparencies, and in addition, radiographic inspection of the relative position of the implant after being inserted can be facilitated.

(c) Since an implant fabricated according to the present invention is basically made of alumina ceramics, the mechanical strength and physical and chemical stability are sufficient and also do not affect the bones or other soft tissues around the implant, having good compatibility therewith. Furthermore, the implant sufficiently tolerates biting stresses thereby suffering no damage or breakage during use and enduring almost perpetually without exchange.

(d) Since the implant is made of ceramics, the surface of the implant has a hydrophilic tendency owing to polarization of the ceramics. It also has good compatibility with or adhesiveness to cells, tissues and bones so that the implant is tightly integrated with the surrounding tissues. In addition thereto, the implant does not give rise to adverse stimulation, poisonousness or carcinogenic possibilities with respect to the surrounding tissues, whereby the possibility of postoperative disease is avoided, making the implant a quite safe dental prosthesis.

As described above, the present invention is a burnt ceramics composition of matter advantageously used as artificial bone, not only in the fields of dentistry and oral surgery as put forth in the examples of the present invention, but also in the field of orthopedics wherein artificial bone is implanted in the bone tissues of a living body.

I claim:

1. A ceramic bone implant comprising:
   (a) 80–90 wt. % $Al_2O_3$; and
   (b) 10–20 wt. % of a compound selected from the group consisting of $La_2O_3$, $Y_2O_3$, and mixtures thereof.

* * * * *